US00PP24972P3

(12) United States Plant Patent

Mehlenbacher et al.

(10) Patent No.: US PP24,972 P3

(45) Date of Patent: Oct. 21, 2014

(54) *CORYLUS* PLANT NAMED 'YORK'

(50) Latin Name: *Corylus avellana*
Varietal Denomination: York

(71) Applicant: State of Oregon acting by and through the State Board of Higher Education on behalf of Oregon State University, Corvallis, OR (US)

(72) Inventors: Shawn A. Mehlenbacher, Corvallis, OR (US); David C. Smith, Corvallis, OR (US); Rebecca L. McCluskey, Corvallis, OR (US)

(73) Assignee: State Board of Higher Education on behalf of Oregon State University, Corvallis, OR (US)

( * ) Notice: Subject to any disclaimer, the term of this patent is extended or adjusted under 35 U.S.C. 154(b) by 50 days.

(21) Appl. No.: 13/694,677

(22) Filed: Dec. 24, 2012

(65) Prior Publication Data

US 2014/0189913 P1 Jul. 3, 2014

(51) Int. Cl.
*A01H 5/00* (2006.01)

(52) U.S. Cl.
USPC ..... Plt./152

(58) Field of Classification Search
USPC ..... Plt./152
See application file for complete search history.

*Primary Examiner* — Anne Grunberg

(74) *Attorney, Agent, or Firm* — Klarquist Sparkman, LLP

(57) ABSTRACT

A new and distinct cultivar of *Corylus* plant named 'York' characterized by globose plant habit and moderate vigor, green developing and fully expanded leaves during the spring and summer, resistance to eastern filbert blight caused by the fungus *Anisogramma anomala* (Peck) E. Müller, presence of random amplified polymorphic DNA markers 152-800 and AA12-850, expression of incompatibility alleles $S_2$ and $S_{21}$ in the styles, and DNA fingerprints at 10 of 23 microsatellite marker loci that differ from both parents OSU 479.027 and OSU 504.065, and from one parent at an additional 11 marker loci.

5 Drawing Sheets

ACKNOWLEDGMENT OF GOVERNMENT SUPPORT

This invention was made with government support under Specific Cooperative Agreement No. 58-5358-4542 awarded by the United States Department of Agriculture. The government has certain rights in the invention.

Botanical denomination: *Corylus avellana*.

Variety designation: 'York'.

BACKGROUND

The present Invention relates to a new and distinct cultivar of *Corylus* plant (hazelnut, filbert), botanically known as *Corylus avellana*, and hereinafter referred to by the name 'York'. *Corylus avellana* is in the family Betulaceae.

The new *Corylus* resulted from a controlled cross of female parent OSU 479.027 (unpatented) and male parent OSU 504.065 (unpatented) made in 1997 by Shawn A. Mehlenbacher and David C. Smith. Hybrid seeds from the cross were harvested in August 1997, stratified, and seedlings grown in the greenhouse during the summer of 1998. From this cross, total of 183 seedling trees were planted in the field in Corvallis, Oreg., USA in October, 1998. 'York' was discovered and selected by the Inventors as a single plant within the progeny of the stated cross-pollination in a controlled environment in Corvallis, Oreg.

'York' was originally assigned the designation OSU 878.048, which indicates the row and tree location of the original seedling. OSU 479.027 is from a cross of OSU 231.111 (unpatented)×OSU 226.122 (unpatented). OSU 504.065 is from a cross of OSU 186.080 (unpatented)×VR 17-15 (unpatented). The pedigree of 'York' includes 'Barcelona' (unpatented) widely grown in Oregon, 'Casina' from Asturias, Spain (unpatented), 'Tonda Gentile delle Langhe' from Piemonte, northern Italy (unpatented), 'Montebello' from Sicily, Italy (unpatented), and 'Tombul Ghiaghli', a Turkish cultivar obtained from Greece (unpatented).

The new cultivar was asexually reproduced by rooted suckers annually for eight years (2003-2010) in Corvallis, Oreg. The new cultivar was also asexually propagated by whip grafting in Corvallis, Oreg. The unique features of this new *Corylus* are stable and reproduced true-to-type in successive generations of asexual reproduction.

SUMMARY

The following traits have been repeatedly observed and are determined to be the unique characteristics of 'York'. These characteristics in combination distinguish 'York' as a new and distinct cultivar:

1. Globose plant habit and moderate vigor.
2. Green developing and fully expanded leaves during the spring and summer.
3. Resistance to eastern filbert blight caused by the fungus *Anisogramma anomala* (Peck) E. Müller.
4. Presence of random amplified polymorphic DNA markers 152-800 and AA12-850 in DNA of 'York' amplified by the polymerase chain reaction. These two markers are linked to a dominant allele for resistance to eastern filbert blight from the cultivar Gasaway (unpatented).
5. Expression of incompatibility alleles $S_2$ and $S_{21}$ in the styles.
6. DNA fingerprints at 10 of 23 microsatellite marker loci differ from both parents OSU 479.027 and OSU 504.065, and from one parent at an additional 11 marker loci. The microsatellite primers are shown in Table 1, and allele sizes are shown in Table 2. DNA fingerprints of standard cultivars 'Barcelona', 'Tonda Gentile delle Langhe' and 'Extra Ghiaghli', and 'Gasaway', the source of eastern filbert blight resistance, are also shown in attached Table 2.

In comparisons in two replicated trials conducted in Corvallis, Oreg., plants of the new *Corylus* differed from plants of the *Corylus avellana* cultivar Barcelona (unpatented), and other cultivars and selections of *Corylus avellana* known to the Inventors primarily in nut size, nut shape, kernel percentage (ratio of kernel weight to nut weight), frequency of blank nuts (nuts lacking kernels), time of pollen shed, time of nut maturity, length of the husk or involucre, and plant size.

BRIEF DESCRIPTION OF THE DRAWINGS

The accompanying colored photographs illustrate the overall appearance of the new cultivar, showing the colors as true as it is reasonably possible to obtain in colored reproductions of this type. Foliage colors in the photographs may differ slightly from the color values cited in the detailed botanical description which accurately describe the colors of the new *Corylus*.

DETAILED BOTANICAL DESCRIPTION

Figure 1:
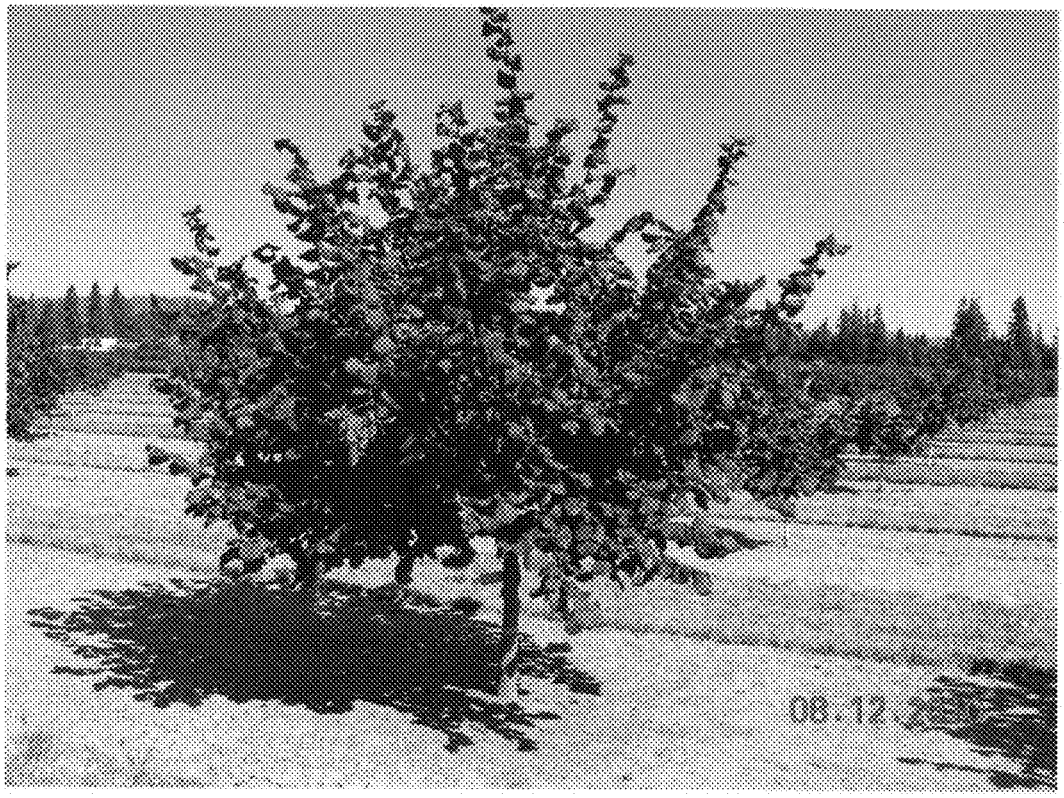
FIG. 1 shows a tree of the new cultivar 'York' growing in a field in August, in Corvallis, Oreg.
Figure 2:
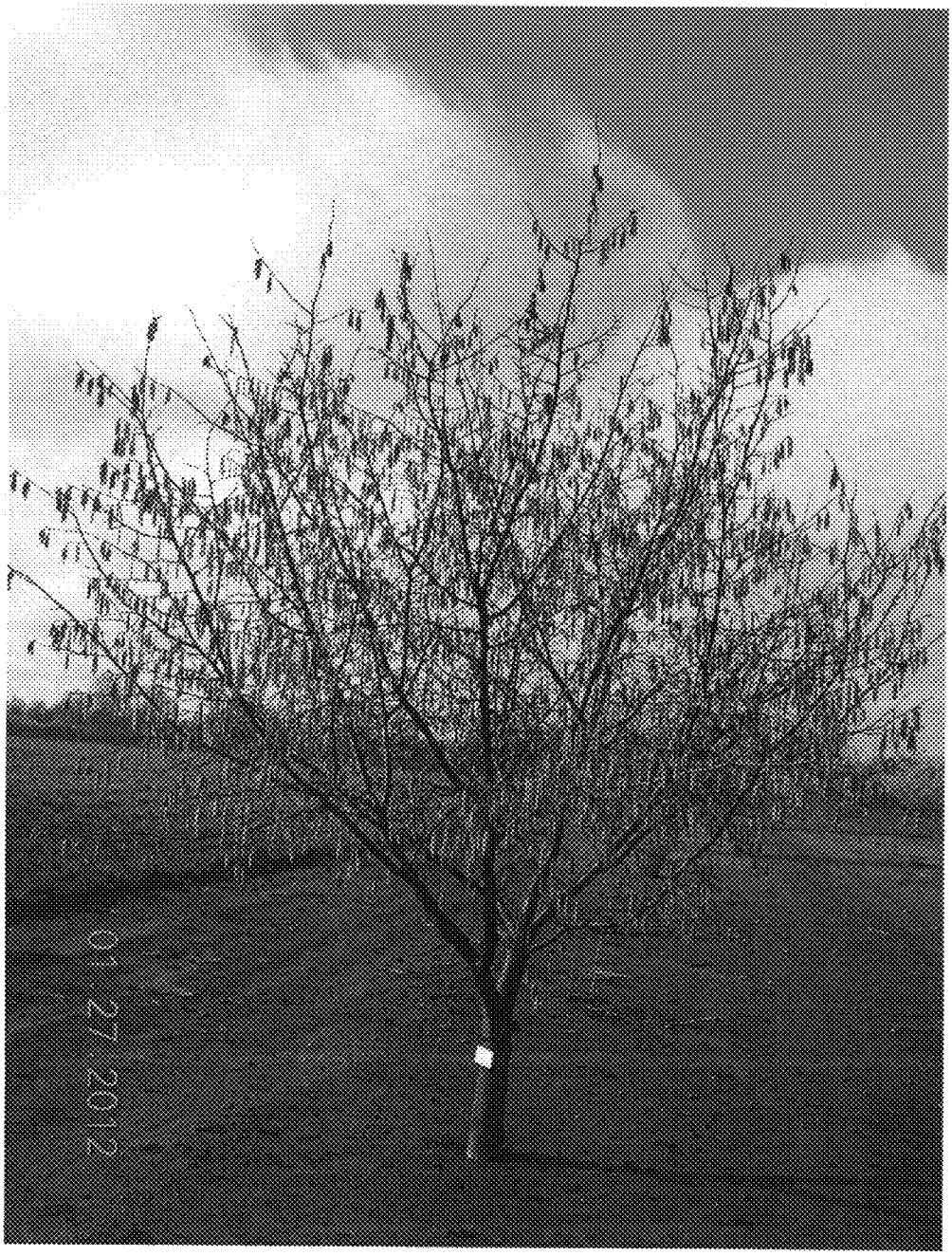
FIG. 2 shows the tree of the new cultivar 'York' growing in a field in January, in Corvallis, Oreg.
Figure 3:
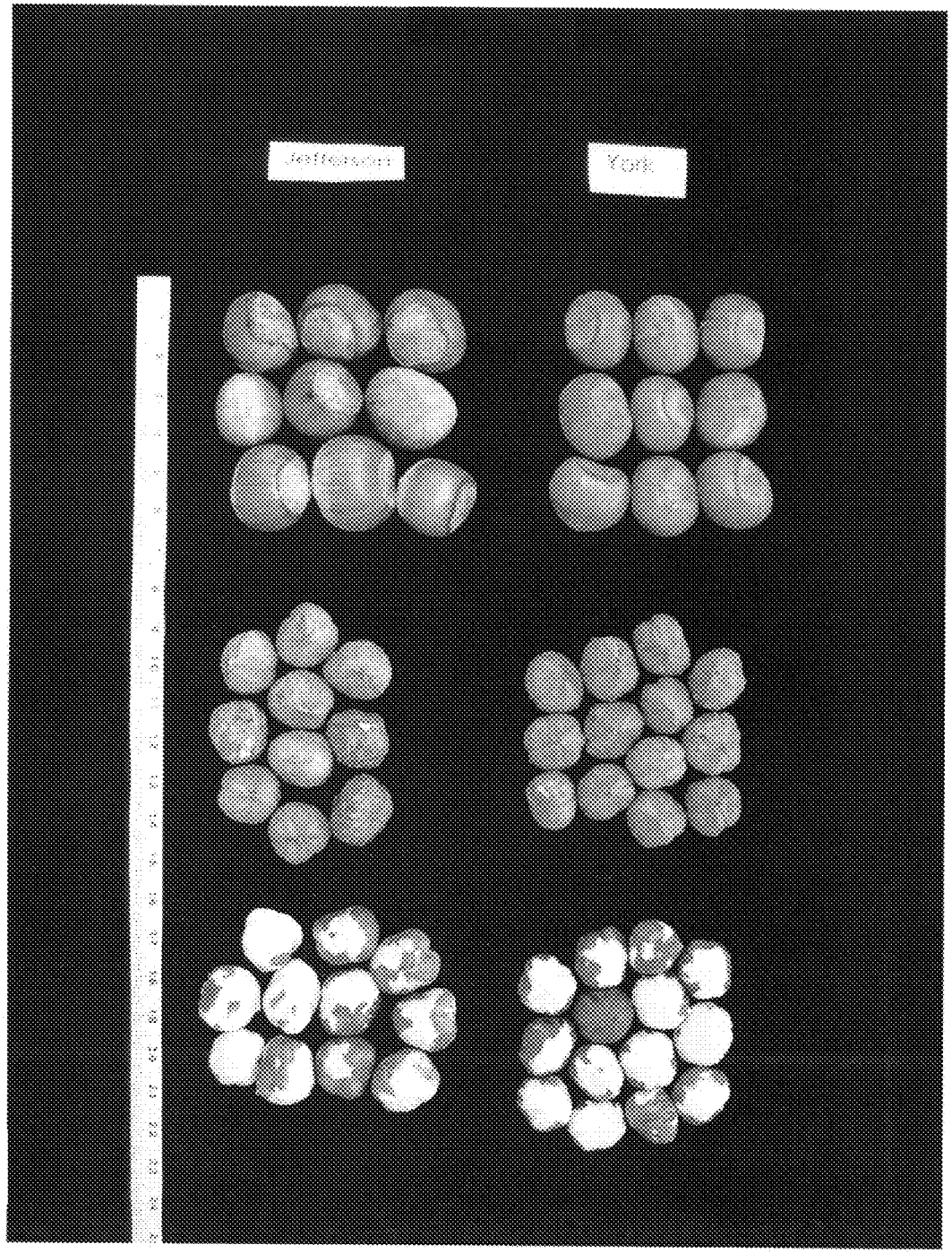
FIG. 3 shows typical nuts, raw kernels, and blanched kernels of 'York' hazelnut compared to those of 'Jefferson' hazelnut.
Figure 4:
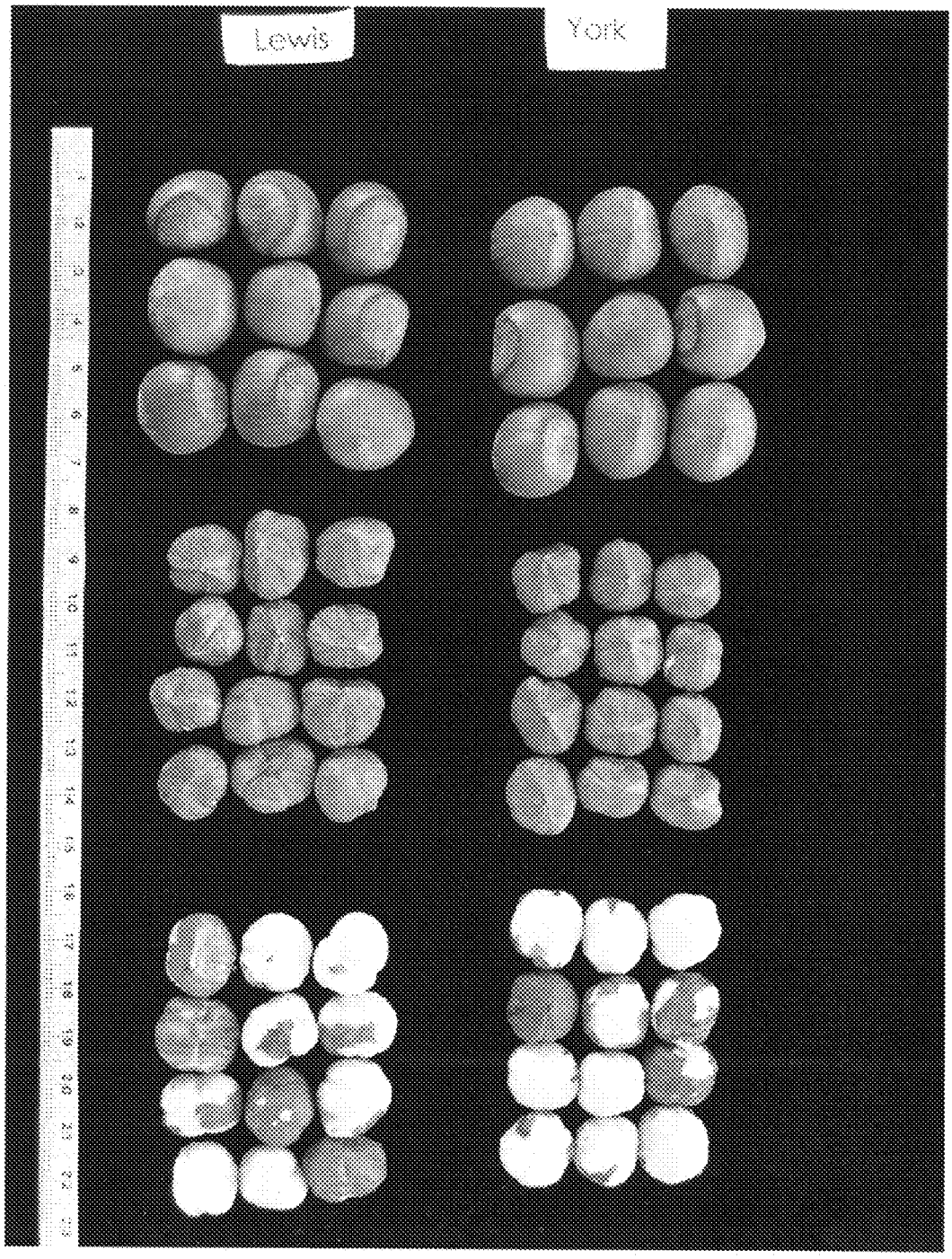
FIG. 4 shows typical nuts, raw kernels, and blanched kernels of 'York' hazelnut compared to those of 'Lewis' hazelnut.
Figure 5:
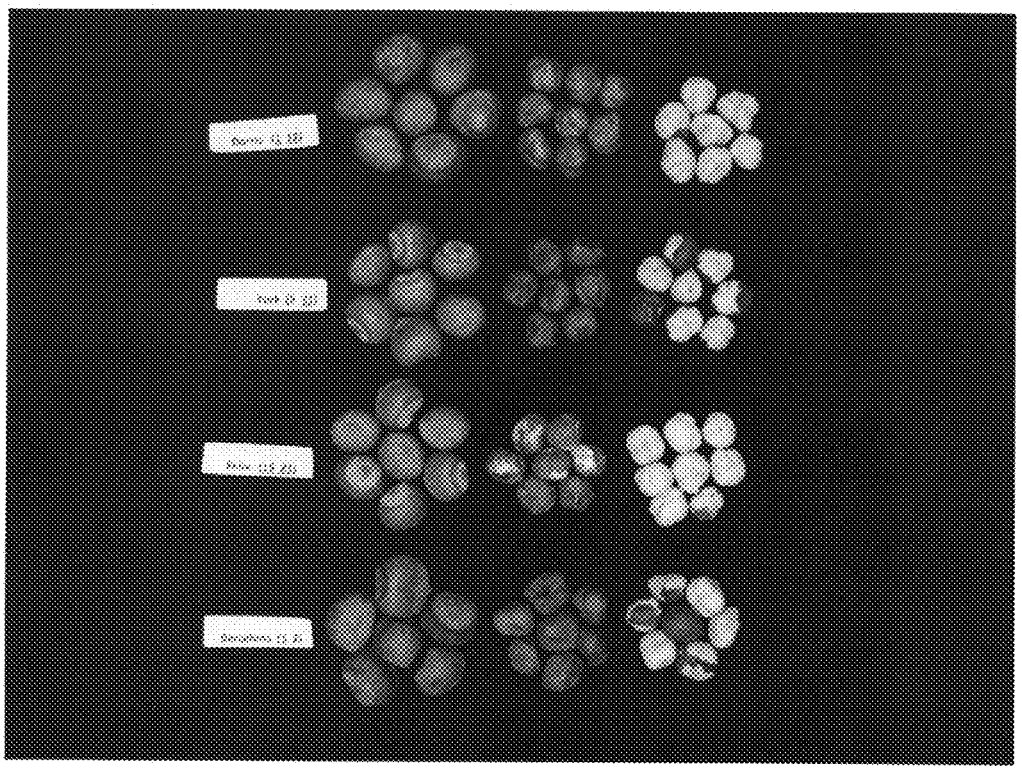
FIG. 5 shows the typical nuts, raw kernels, and blanched kernels of 'York' hazelnut compared to those of 'Barcelona' hazelnut and other hazelnut cultivars.

The cultivar York has not been observed under all possible environmental conditions. The phenotype may vary somewhat with variations in environment such as temperature and light intensity, without, however, any variance in genotype. The aforementioned photographs and following observations and measurements describe plants grown in Corvallis, Oreg. under commercial practice outdoors in the field during the fall, winter and spring. Plants used for the photographs and description were propagated by tie-off layerage and growing on their own roots, and about seven years old. In the following description, color references are made to The Royal Horticultural Society Colour Chart, 1966 Edition, except where general terms of ordinary dictionary significance are used.

Botanical classification: *Corylus avellana* cultivar York.

Parentage:

- *Female, or seed, parent.*—*Corylus avellana* selection OSU 479.027 (unpatented).
- *Male, or pollen, parent.*—*Corylus avellana* selection OSU 504.065 (unpatented).

Propagation (type rooted suckers):

- *Time to initiate roots.*—About 30 days at 20 degrees C.
- *Time to produce a rooted young plant.*—About six months at 22 degrees C.
- *Root description.*—Fine to thick; freely branching; creamy white in color.

Propagation (type whip grafting):

- *Time to budbreak on the scions.*—About 14 days at 25° C.
- *Time to produce a grafted plant.*—About six months at 25° C.

Plant description:

- *General appearance.*—Perennial shrub.
- *Size.*—Plant height is about 5 meters; plant diameter or spread is about 5 meters.
- *Form.*—Spreading plant habit.
- *Growth and branching habit.*—freely branching; about 15 lateral branches develop per plant. Pinching, i.e., removal of the terminal apices, enhances branching with lateral branches potentially forming at every node.
- *Vigor.*—Moderate vigor growth habit.
- *Roots.*—Fine to thick; freely branching; creamy white in color.
- *Lenticels.*—11 circular within 1 square centimeter (counted on dormant scions).

Lateral branch description:

- *Length.*—About 38 cm.
- *Diameter.*—About 6 mm.
- *Internode length.*—About 3.2 cm.
- *Texture.*—Smooth, glabrous.
- *Strength.*—Strong.
- *Color.*—Immature — 152B, mature — 152B.

Foliage description:

- *Arrangement.*—Alternate, simple
- *Length.*—About 10.0 cm.
- *Width.*—About 9.3 cm.
- *Shape.*—Ablong to ovate.
- *Apex.*—Obtuse to acute.
- *Base.*—Cordate.
- *Margin.*—Serrate.
- *Texture.*—Upper and lower surfaces — slightly pubescent.
- *Venation pattern.*—Pinnate.
- *Leaf bud shape.*—Globular.
- *Time of leaf bud burst.*—Midseason, 11 days after 'Barcelona'.
- *Color.*—Developing foliage: upper surface 146B, lower surfaces: 146C. Fully expanded foliage, upper surface: Spring and summer, 146A; late summer and fall, 146A. Fully expanded foliage, lower surface: Spring and summer, 146C; late summer and fall, 146C. Venation, upper surface: Spring and summer, 146A; late summer and fall, 146A. Venation, lower surface: Spring and summer, 148D; late summer and fall, 148D. Leaf bud, 177C.

Petiole description:

- *Length.*—About 2.7 cm.
- *Diameter.*—About 1.8 mm.
- *Texture.*—Upper and lower surfaces: pubescent.
- *Color.*—Upper surface: Spring and summer, 139D; late summer and fall, 139D. lower surface: Spring and summer, 139D; late summer and fall, 139D.

Flower description:

- *Male inflorescences.*—Catkins, color prior to elongation 194C.
- *Female inflorescence.*—Style color 047B.
- *Stigma coloration.*—047B.
- *Time of female flowering.*—Midseason, 14 days after 'Barcelona'.

*Time of pollen shed*.—Midseason, around the same time as 'Daviana' (unpatented).

Involcure description:

*Involucre constriction*.—Absent.

*Involucre length*.—25% longer than nuts.

*Strength of serration of indentation*.—Moderate.

*Pubescence*.—Little

*Thickness of callus at base*.—Moderate callus at base similar to 'Barcelona'.

*Description of jointing of bracts*.—Involucre slit to the base on one side. Nuts fall free of the involucre at maturity (95% fall free).

Nut description:

*Length*.—About 18.0 mm

*Width*.—About 19.7 mm.

*Depth*.—About 17.0 mm.

*Nut shape*.—Round.

*Nut shape index [(width+depth)/2*length]*.—1.02.

*Nut compression index* (*width/depth*).—1.16.

*Nut shell color*.—164A.

*Nut weight*.—About 2.73 grams to 2.85 grams.

*Predominant number of fruits per cluster*.—Average 2 nuts per cluster.

*Stripes on shell*.—About 24, color slightly darker than 164A.

*Fruit apex*.—Slight (not prominent).

*Size of the fruit pistil scar*.—Very small (0.5 mm×1 mm).

*Nut curvature of the basal scar*.—Flat (plane).

*Frequency of blank nuts*.—9.7%.

*Time of nut maturity*.—About 3 days earlier that 'Barcelona'.

*Husk length*.—About 25% longer than the nuts.

*Kernel weight*.—About 1.23 grams to 1.32 grams.

*Kernel percentage* (*kernel weight/nut weight*).—About 46%. Kernel shape — globular.

*Kernel cross section shape*.—Circular.

*Kernel base shape*.—Flat.

*Lateral grooves*.—None.

Disease/pest resistance: Plants of the new *Corylus* are highly resistant to eastern filbert blight caused by the fungus *Anisogramma anomala* (Peck) E. Müller. Plants of the new *Corylus* are highly resistant to bud mites (*Phytoptus avellanae* Nal.), while plants of 'Tonda Gentile delle Langhe' are highly susceptible, and plants of 'Barcelona' are highly resistant.

Temperature tolerance: Tolerates temperatures from −10 to 38° C. in the field in Corvallis, Oreg.

TABLE 1

Primers and annealing temperatures for the 24 microsatellite marker loci used to fingerprint 'York' and other hazelnut cultivars.

| Locus | Repeat motif | Size | $T_a$ | n | He | Ho |
|---|---|---|---|---|---|---|
| A613 | $(TC)_{13}(CA)_{12}$ | 149-177 | 60 | 14 | 0.85 | 0.85 |
| A614 | $(TC)_{17}(CA)_{10}$ NNN$(CA)_6$ | 125-156 | 60 | 14 | 0.85 | 0.85 |
| A616 | $(AC)_{11}$ | 136-162 | 60 | 13 | 0.85 | 0.85 |
| A640 | $(CT)_{15}$ $(CA)_{13}$ | 354-378 | 67 | 11 | 0.80 | 0.73 |
| B107 | $(CT)_{14}$ | 112-151 | 55 | 14 | 0.85 | 0.80 |
| B617 | $(GA)_{15}$ | 280-298 | 60 | 9 | 0.80 | 0.78 |
| B619 | $(TC)_{21}$ | 146-180 | 60 | 14 | 0.88 | 0.88 |
| B634 | $(AG)_{15}$ | 218-238 | 60 | 9 | 0.76 | 0.76 |

TABLE 1-continued

Primers and annealing temperatures for the 24 microsatellite marker loci used to fingerprint 'York' and other hazelnut cultivars.

| | | | | | | |
|---|---|---|---|---|---|---|
| B657 | $(AG)_{15}$ | 210-228 | 60 | 8 | 0.84 | 0.98 |
| B671 | $(AG)_6$NN $(GA)_{17}$ | 221-249 | 60 | 13 | 0.86 | 0.88 |
| B709 | $(GA)_{21}$ | 219-233 | 60 | 8 | 0.74 | 0.76 |
| B733 | $(TC)_{15}$ | 161-183 | 60 | 8 | 0.68 | 0.68 |
| B741 | $(GT)_5(GA)_{12}$ | 176-194 | 60 | 10 | 0.77 | 0.78 |
| B749 | $(TC)_{12}$ | 200-210 | 60 | 6 | 0.60 | 0.64 |
| B751 | $(GA)_{15}$ | 141-153 | 60 | 7 | 0.80 | 0.80 |
| B774 | $(AG)_{15}$ | 195-213 | 60 | 8 | 0.80 | 0.80 |
| B776 | $(GA)_{17}$ | 134-148 | 60 | 7 | 0.71 | 0.60 |
| B795 | $(TC)_8$Ns$(CT)_7$ Ns$(CT)_{10}$ Ns$(TC)_5$ | 296-332 | 60 | 12 | 0.76 | 0.74 |
| C115 | $(TAA)_5$ $(GAA)_{12}$ | 167-226 | 60 | 14 | 0.80 | 0.80 |
| KG809 | $(AGG)_6$ | 333-345 | 55 | 5 | 0.66 | 0.64 |
| KG811 | $(GA)_{17}$ | 240-278 | 58 | 12 | 0.83 | 0.82 |
| KG827 | $(CT)_{13}$AA $(CA)_7$ | 264-282 | 67 | 9 | 0.78 | 0.84 |
| KG830 | $(CT)_{14}$ GTATT $(CA)_8$ | 279-311 | 67 | 9 | 0.79 | 0.78 |
| Soman-G | $(AAT)_5$ | | 54 | 3 | 0.60 | 0.98 |

| Locus | PIC | r | LG | Primers 5'-3' |
|---|---|---|---|---|
| A613 | 0.85 | 0.00 | 11 | Ned-CACACGCCTT GTCACTCTTT (SEQ ID NO: 1) |
| A614 | 0.84 | 0.00 | 6 | Hex-TGGCAGAGCT TTGTCAGCTT (SEQ ID NO: 3) |
| A616 | 0.83 | 0.00 | 8 | Fam-CACTCATACC GCAAACTCCA (SEQ ID NO: 5) |
| A640 | 0.7 | 0.04 | 10 | F-TGCCTCTGCA GTTAGTCATC AAATGTAGG (SEQ ID NO: 7) |
| B107 | 0.83 | 0.02 | 10 | Ned-GTAGGTGCAC TTGATGTGCTT TAC (SEQ ID NO: 9) |
| B617 | 0.78 | 0.01 | 8 | Fam-TCCGTGTTGA GTATGGACGA (SEQ ID NO: 11) |
| B619 | 0.7 | 0.00 | 3 | Fam-AGTCGGCTCC CCTTTTCTC (SEQ ID NO: 13) |
| B634 | 0.73 | 0.00 | 4 | Hex-CCTGCATCCA GGACTCATTA 60 (SEQ ID NO: 15) |
| B657 | 0.82 | −0.08 | 11 | Ned-GAGAGTGCGT CTTCCTCTGG (SEQ ID NO: 17) |
| B671 | 0.84 | −0.01 | 9 | Hex-TTGCCAGTGC ATACTCTGAT G (SEQ ID NO: 19) |
| B709 | 0.70 | −0.01 | 5 | Ned-CCAAGCACGA ATGAACTCAA (SEQ ID NO: 21) |
| B733 | 0.63 | 0.00 | 7.2 | Ned-CACCCTCTTCA CCACCTCAT (SEQ ID NO: 23) |
| B741 | 0.74 | 0.00 | 5 | Fam-GTTCACAGGC TGTTGGGTTT (SEQ ID NO: 25) |
| B749 | 0.51 | −0.03 | 1 | Hex-GGCTGACAAC ACAGCAGAAA (SEQ ID NO: 27) |
| B751 | 0.77 | 0.01 | 7.2 | Fam-AGCTGGTTCTT CGACATTCC (SEQ ID NO: 29) |

TABLE 1-continued

Primers and annealing temperatures for the 24 microsatellite marker loci used to fingerprint 'York' and other hazelnut cultivars.

| | | | | |
|---|---|---|---|---|
| B774 | 0.77 | 0.01 | 5 | Ned-GTTTTGCGAG CTCATTGTCA (SEQ ID NO: 31) |
| B776 | 0.67 | 0.07 | 6 | Fam-TGTATGTACA CACGGAGAGA GAGA (SEQ ID NO: 33) |
| B795 | 0.74 | 0.01 | NA | Fam-GACCCACAAA CAATAACCTA TCTC (SEQ ID NO: 35) |
| C115 | 0.77 | 0.00 | 4 | Fam-ATTTTCCGCA GATAATACAGG (SEQ ID NO: 37) |
| KG809 | 0.60 | 0.01 | 4 | Hex-AGGCATCAGT TCATCCAA (SEQ ID NO: 39) |
| KG811 | 0.81 | 0.01 | 2 | Ned-AAGGCGGCAC TCGCTCAC (SEQ ID NO: 41) |
| KG827 | 0.75 | −0.04 | 9 | Fam-AGAACTCCGA CTAATAATCC TAACCCTTGC (SEQ ID NO: 43) |
| KG830 | 0.76 | 0.00 | 9 | Ned-TGGAGGAAGT TTTGAATGGT AGTAGAGGA (SEQ ID NO: 45) |
| Soman-G | 0.51 | −0.27 | NA | Hex-TGGCGTTGCA ACATATTCTC (SEQ ID NO: 47) |

| Locus | Primers 5'-3' | Reference |
|---|---|---|
| A613 | R-CCCCTTTCACAT GTTTGCTT (SEQ ID NO: 2) | Gurcan et al. 2010 |
| A614 | R-GCAGTGGAGGA TTGCTGACT (SEQ ID NO: 4) | Gurcan et al. 2010 |
| A616 | R-ATGGCTTTTGCT TCGTTTTG (SEQ ID NO: 6) | Gurcan et al. 2010 |
| A640 | Fam-CGCCATATAATT GGGATGCTTGTT G (SEQ ID NO: 8) | Gurcan et al. 2010 |
| B107 | R-AACACCATATTG AGTCTTTCAAAG C (SEQ ID NO: 10) | Boccacci et al. 2005; Gokirmak et al. 2009 |
| B617 | R TGTTTTTGGTGG AGCGATG (SEQ ID NO: 12) | Gurcan et al. 2010 |
| B619 | R-GCGATCTGACCT CATTTTTG (SEQ ID NO: 14) | Gurcan et al. 2010 |
| B634 | R-GTGCAGAGGTTG CACTCAAA (SEQ ID NO: 16) | Gurcan et al. 2010 |
| B657 | R-AGCCTCACCTCC AACGAAC (SEQ ID NO: 18) | Gurcan et al. 2010 |
| B671 | R-ACCAGCTCTGGG CTTAACAC (SEQ ID NO: 20) | Gurcan et al. 2010 |
| B709 | R-GCGGGTTCTCGT TGTACACT (SEQ ID NO: 22) | Gurcan et al. 2010 |
| B733 | R-CATCCCCTGTTG GAGTTTTC (SEQ ID NO: 24) | Gurcan et al. 2010 |
| B741 | R-CGTGTTGCTCAT GTGTTGTG (SEQ ID NO: 26) | Gurcan et al. 2010 |

TABLE 1-continued

Primers and annealing temperatures for the 24 microsatellite marker loci used to fingerprint 'York' and other hazelnut cultivars.

| | | |
|---|---|---|
| B749 | R-TCGGCTAGGGTT AGGGTTTT (SEQ ID NO: 28 | Gurcan et al. 2010 |
| B751 | R-AAACTCAAATA AAACCCCTGCTC (SEQ ID NO: 30) | Gurcan et al. 2010 |
| B774 | R-TGTGTGTGGTCT GTAGGCACT (SEQ ID NO: 32) | Gurcan et al. 2010 |
| B776 | R-TGAGGGGAAGA GGTTTGATG (SEQ ID NO: 34) | Gurcan et al. 2010 |
| B795 | R-TGGGCATCATCC AGGTCTA (SEQ ID NO: 36) | Gurcan et al. 2010 |
| C115 | GTTTCCAGATCT GCCTCCATATAA T (SEQ ID NO: 38) | Bassil et al. 2005b, Gokirmak et al. 2009 |
| KG809 | F-GGAAGGTGAGA GAAATCAAGT (SEQ ID NO: 40) | Gurcan and Mehlenbacher 2010 |
| KG811 | F-GAACAACTGAA GACAGCAAAG (SEQ ID NO: 42) | Gurcan and Mehlenbacher 2010 |
| KG827 | GAGGGAGCAAQ TCAAAGTTGAGA AGAAA (SEQ ID NO: 44) | Gurcan and Mehlenbacher 2010 |
| KG830 | AAAGCAACTCAT AGCTGAAGTCCA ATCA (SEQ ID NO: 46) | Gurcan and Mehlenbacher 2010 |
| Soman-G | R-GCCATCTTTAGA AAGTTCGATACAG (SEQ ID NO: 48) | unpublished |

Primer fluorescent tags are FAM, HEX, and NED.
Ta: annealing temperature (° C.)
N: number of alleles
He: expected heterozygosity
Ho: observed heterozygosity
PIC: polymorphism information content
r: estimated null allele frequency
LG: linkage group

TABLE 2

Allele sizes in 'York', its parents, and four other hazelnut cultivars at 24 microsatellite loci.

| Tag | Locus | 'York' | 479.027 | 504.065 | 'Tonda Gentile delle Langhe' |
|---|---|---|---|---|---|
| NED | A613 | 157/177 | 177/177 | 157/159 | 151/157 |
| HEX | A614 | 125/158 | 125/132 | 148/158 | 125/135 |
| FAM | A616 | 142/150 | 142/150 | 150/150 | 148/150 |
| FAM | A640 | 362/374 | 354/374 | 354/362 | 354/368 |
| NED | B107 | 122/134 | 134/146 | 122/134 | 134/152 |
| FAM | B617 | 286/290 | 286/290 | 286/286 | 286/296 |
| FAM | B619 | 156/164 | 156/164 | 156/164 | 148/164 |
| HEX | B634 | 226/234 | 226/226 | 232/234 | 226/226 |
| NED | B657 | 220/222 | 222/226 | 220/224 | 218/226 |
| HEX | B671 | 241/247 | 227/247 | 241/241 | 237/241 |
| NED | B709 | 227/231 | 227/231 | 227/227 | 227/227 |
| NED | B733 | 171/179 | 171/179 | 173/179 | 171/173 |
| FAM | B741 | 177/186 | 177/186 | 177/184 | 177/184 |
| HEX | B749 | 208/208 | 206/208 | 206/208 | 206/208 |
| FAM | B751 | 151/153 | 151/153 | 143/151 | 149/153 |
| NED | B774 | 203/209 | 209/211 | 203/207 | 203/211 |
| FAM | B776 | 137/150 | 137/137 | 137/150 | 137/137 |
| FAM | B795 | 330/330 | 296/330 | 330/330 | 312/330 |
| FAM | C115 | 197/197 | 194/197 | 194/197 | 173/173 |

TABLE 2-continued

Allele sizes in 'York', its parents, and four other hazelnut cultivars at 24 microsatellite loci.

| | | | | | |
|---|---|---|---|---|---|
| HEX | KG809 | 336/345 | 336/339 | 339/345 | 336/339 |
| NED | KG811 | 254/254 | 254/254 | 254/264 | 254/264 |
| FAM | KG827 | 266/270 | 270/282 | 266/266 | 266/268 |
| NED | KG830 | 295/295 | 295/295 | 295/295 | 291/295 |
| HEX | SMNG | 196/200 | 196/200 | 196/200 | 196/200 |

| Tag | Locus | 'Barcelona' | 'Extra Ghiaghli' | 'Gasaway' |
|---|---|---|---|---|
| NED | A613 | 151/159 | 167/169 | 159/161 |
| HEX | A614 | 125/131 | 125/150 | 143/158 |
| FAM | A616 | 142/150 | 150/158 | 148/148 |
| FAM | A640 | 354/374 | 374/374 | 362/368 |
| NED | B107 | 112/134 | 116/116 | 122/128 |
| FAM | B617 | 286/290 | 294/296 | 292/296 |
| FAM | B619 | 156/170 | 164/174 | 170/174 |
| HEX | B634 | 226/226 | 226/226 | 220/232 |
| NED | B657 | 218/222 | 210/222 | 224/228 |
| HEX | B671 | 223/227 | 227/247 | 235/247 |
| NED | B709 | 225/233 | 225/227 | 227/227 |
| NED | B733 | 171/173 | 171/171 | 173/173 |
| FAM | B741 | 177/186 | 177/184 | 186/188 |
| HEX | B749 | 208/208 | 208/208 | 206/208 |
| FAM | B751 | 143/153 | 143/147 | 143/143 |
| NED | B774 | 203/207 | 195/203 | 203/209 |
| FAM | B776 | 135/137 | 135/137 | 146/150 |
| FAM | B795 | 330/330 | 296/310 | 314/316 |
| FAM | C115 | 173/194 | 182/194 | 215/218 |
| HEX | KG809 | 336/336 | 336/339 | 336/345 |
| NED | KG811 | 258/264 | 240/242 | 254/258 |
| FAM | KG827 | 280/282 | 276/282 | 270/280 |
| NED | KG830 | 291/295 | 291/295 | 291/305 |
| HEX | SMNG | 196/200 | 196/200 | 196/196 |

REFERENCES:

Bassil N. V., Botta R., Mehlenbacher S. A. 2005a. Microsatellite markers in hazelnut: Isolation, characterization and cross-species amplification. J. Amer. Soc. Hort. Sci. 130: 543-549.

Bassil N. V., Botta R., Mehlenbacher S. A. 2005b. Additional microsatellite markers of the European hazelnut. Acta Hort. 686:105-110.

Boccacci P., Akkak A., Bassil N. V., Mehlenbacher S. A., Botta R. 2005. Characterization and evaluation of microsatellite loci in European hazelnut (*C. avellana*) and their transferability to other *Corylus* species. Molec. Ecol. Notes 5:934-937.

Boccacci P., Akkak, A. and Botta, R. 2006. DNA typing and genetic relations among European hazelnut (*Corylus avellana* L.) cultivars using microsatellite markers. Genome 49:598-611.

Gökirmak T , Mehlenbacher S. A., Bassil N. V. 2009. Characterization of European hazelnut (*Corylus avellana*) cultivars using SSR markers. Genetic Resources and Crop Evolution 56:147-172.

Gürcan, K., S. A. Mehlenbacher and V. Erdogan. 2010a. Genetic diversity in hazelnut cultivars from Black Sea countries assessed using SSR markers. Plant Breeding (available on-line doi:10.1111/j.1439-0523.2009.01753.x).

Gürcan, K., S. A. Mehlenbacher, N. V. Bassil, P. Boccacci, A. Akkak and R. Botta. 2010b. New microsatellite markers for *Corylus avellana* from enriched libraries. Tree Genetics and Genomes (available on-line as DOI 10.1007/s11295-010-0269-y).

Gürcan, K. and S. A. Mehlenbacher. 2010. Development of microsatellite marker loci for European hazelnut (*Corylus avellana* L.) from ISSR fragments. Molecular Breeding (available on-line).

SEQUENCE LISTING

```
<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1

cacacgcctt gtcactcttt                                                20


<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2

ccccttttcac atgtttgctt                                               20


<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide
```

-continued

<400> SEQUENCE: 3 tggcagagct ttgtcagctt 20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4 gcagtggagg attgctgact 20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5 cactcatacc gcaaactcca 20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6 atggcttttg cttcgttttg 20

<210> SEQ ID NO 7
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 7 tgcctctgca gttagtcatc aaatgtagg 29

<210> SEQ ID NO 8
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 8 cgccatataa ttgggatgct tgttg 25

<210> SEQ ID NO 9
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 9 gtaggtgcac ttgatgtgct ttac 24

-continued

<210> SEQ ID NO 10
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 10 aacaccatat tgagtctttc aaagc 25

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11 tccgtgttga gtatggacga 20

<210> SEQ ID NO 12
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 12 tgtttttggt ggagcgatg 19

<210> SEQ ID NO 13
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 13 agtcggctcc ccttttctc 19

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14 gcgatctgac ctcatttttg 20

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15 cctgcatcca ggactcatta 20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide -continued

<400> SEQUENCE: 16 gtgcagaggt tgcactcaaa 20

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17 gagagtgcgt cttcctctgg 20

<210> SEQ ID NO 18
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 18 agcctcacct ccaacgaac 19

<210> SEQ ID NO 19
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 19 ttgccagtgc atactctgat g 21

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20 accagctctg ggcttaacac 20

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21 ccaagcacga atgaactcaa 20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22 gcgggttctc gttgtacact 20

-continued

<210> SEQ ID NO 23
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 23 caccctcttc accacctcat 20

<210> SEQ ID NO 24
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 24 catcccctgt tggagttttc 20

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25 gttcacaggc tgttgggttt 20

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26 cgtgttgctc atgtgttgtg 20

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27 ggctgacaac acagcagaaa 20

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28 tcggctaggg ttagggtttt 20

<210> SEQ ID NO 29
<211> LENGTH: 20
<212> TYPE: DNA
<213> ORGANISM: Artificial Sequence
<220> FEATURE:
<223> OTHER INFORMATION: Synthetic polynucleotide -continued

<400> SEQUENCE: 29 agctggttct tcgacattcc 20

<210> SEQ ID NO 30
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 30 aaactcaaat aaaacccctg ctc 23

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31 gttttgcgag ctcattgtca 20

<210> SEQ ID NO 32
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 32 tgtgtgtggt ctgtaggcac t 21

<210> SEQ ID NO 33
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 33 tgtatgtaca cacggagaga gaga 24

<210> SEQ ID NO 34
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 34 tgaggggaag aggtttgatg 20

<210> SEQ ID NO 35
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 35 gacccacaaa caataaccta tctc 24

-continued

<210> SEQ ID NO 36
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 36 tgggcatcat ccaggtcta 19

<210> SEQ ID NO 37
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 37 attttccgca gataatacag g 21

<210> SEQ ID NO 38
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 38 gtttccagat ctgcctccat ataat 25

<210> SEQ ID NO 39
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 39 aggcatcagt tcatccaa 18

<210> SEQ ID NO 40
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 40 ggaaggtgag agaaatcaag t 21

<210> SEQ ID NO 41
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 41 aaggcggcac tcgctcac 18

<210> SEQ ID NO 42
<211> LENGTH: 21
<212> TYPE: DNA
<213> ORGANISM: Artificial Sequence
<220> FEATURE:
<223> OTHER INFORMATION: Synthetic polynucleotide -continued

<400> SEQUENCE: 42 gaacaactga agacagcaaa g 21

<210> SEQ ID NO 43
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 43 agaactccga ctaataatcc taacccttgc 30

<210> SEQ ID NO 44
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 44 gagggagcaa gtcaaagttg agaagaaa 28

<210> SEQ ID NO 45
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 45 tggaggaagt tttgaatggt agtagagga 29

<210> SEQ ID NO 46
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 46 aaagcaactc atagctgaag tccaatca 28

<210> SEQ ID NO 47
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 47 tggcgttgca acatattctc 20

<210> SEQ ID NO 48
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 48 gccatcttta gaaagttcga tacag 25

We claim:

1. A new and distinct cultivar of *Corylus* plant named 'York', as illustrated and described.

* * * * *